United States Patent
Funk (10) Patent No.: US 11,213,371 B2
(45) Date of Patent: Jan. 4, 2022

(54) SCAN ABUTMENT HAVING AN ENLARGED SCAN SURFACE

(71) Applicant: KULZER GMBH, Hanau (DE)

(72) Inventor: Matthias Funk, Hanau (DE)

(73) Assignee: KULZER GMBH, Hanau (DE)

(*) Notice: Subject to any disclaimer, the term of this patent is extended or adjusted under 35 U.S.C. 154(b) by 503 days.

(21) Appl. No.: 15/771,473

(22) PCT Filed: Oct. 26, 2016

(86) PCT No.: PCT/EP2016/075795
§ 371 (c)(1),
(2) Date: Apr. 27, 2018

(87) PCT Pub. No.: WO2017/072171
PCT Pub. Date: May 4, 2017

(65) Prior Publication Data
US 2018/0303584 A1    Oct. 25, 2018

(30) Foreign Application Priority Data
Oct. 27, 2015  (DE) .................... 10 2015 118 285.8

(51) Int. Cl.
*A61C 8/00*    (2006.01)
*A61C 9/00*    (2006.01)
(Continued)

(52) U.S. Cl.
CPC .......... *A61C 8/0001* (2013.01); *A61C 8/0012* (2013.01); *A61C 8/0039* (2013.01);
(Continued)

(58) Field of Classification Search
CPC ... A61C 8/0012; A61C 8/0039; A61C 8/0048; A61C 13/0004; A61C 9/004
(Continued)

(56) References Cited

U.S. PATENT DOCUMENTS 5,782,918 A * 7/1998 Klardie ............... A61C 8/0066
606/60
6,168,436 B1 * 1/2001 O'Brien ............... A61C 8/005
433/172
(Continued)

FOREIGN PATENT DOCUMENTS

CN       204484369 U    7/2015
DE    102008028214 A1   12/2009
(Continued)

*Primary Examiner* — Matthew M Nelson
(74) *Attorney, Agent, or Firm* — Norris McLaughlin, P.A.

(57) ABSTRACT

The invention relates to a scan abutment (2) for determination of the position of the plane of the front face (1.1) of a dental endosseous implant (1), wherein the abutment (2) has a longish, hollow shaft (4) and a base (3) at the bottom side (4.2) of the shaft (4), and the base (3) with at least a part of its bottom side (8.2) is attachable onto the front face (1.1) of the implant (1), wherein the base (3) has a recess (9) extending from the upper side (8.1) to the lower side (8.2) of the base (3), wherein the longish, hollow shaft (4) has from a side wall (10) having at least one through hole (5a) at its outer periphery, wherein the through hole of the side wall (10) extends from the bottom side (4.2) of the shaft (4) to the upper side (4.1) of the shaft, thereby forming a planar surface (6) in the plane (12) between shaft (4) and base (3).

15 Claims, 5 Drawing Sheets

(51) Int. Cl.
*A61K 6/84* (2020.01)
*A61K 6/90* (2020.01)
*A61K 6/844* (2020.01)
*A61K 6/887* (2020.01)
*A61K 6/891* (2020.01)
*A61C 13/00* (2006.01)

(52) U.S. Cl.
CPC ............ *A61C 8/0048* (2013.01); *A61C 9/004* (2013.01); *A61C 13/0004* (2013.01); *A61K 6/84* (2020.01); *A61K 6/844* (2020.01); *A61K 6/887* (2020.01); *A61K 6/891* (2020.01); *A61K 6/90* (2020.01)

(58) Field of Classification Search
USPC .......................................................... 433/173
See application file for complete search history.

(56) References Cited

U.S. PATENT DOCUMENTS

| | | | | |
|---|---|---|---|---|
| 2001/0053512 A1* | 12/2001 | Nichinonni | ............ | A61C 8/005 433/173 |
| 2004/0063062 A1* | 4/2004 | Brajnovic | ............ | A61C 8/0001 433/75 |
| 2004/0096804 A1* | 5/2004 | Vogt | ...................... | A61C 8/0087 433/173 |
| 2006/0014120 A1* | 1/2006 | Sapian | .................. | A61C 8/0065 433/173 |
| 2006/0217738 A1* | 9/2006 | Tanimura | ............... | A61C 8/005 606/104 |
| 2006/0257811 A1* | 11/2006 | Ohki | ........................ | A61C 8/00 433/18 |
| 2007/0054241 A1* | 3/2007 | Kim | ...................... | A61C 8/0048 433/173 |
| 2007/0111162 A1* | 5/2007 | Laux | .................... | A61C 8/0048 433/173 |
| 2010/0196852 A1* | 8/2010 | Baruc | .................... | A61C 8/005 433/173 |
| 2010/0209877 A1* | 8/2010 | Hogan | ................. | A61C 8/0001 433/214 |
| 2011/0129798 A1* | 6/2011 | Zucker | ................. | A61C 8/0001 433/173 |
| 2012/0122056 A1* | 5/2012 | Kim | ...................... | A61C 8/0068 433/173 |
| 2012/0264082 A1* | 10/2012 | Segura | ................. | A61C 8/0048 433/174 |
| 2013/0309632 A1* | 11/2013 | Sanders | ............... | A61C 8/0022 433/174 |
| 2014/0141387 A1* | 5/2014 | Kikuchi | ............... | A61C 8/0081 433/174 |
| 2014/0178835 A1* | 6/2014 | Lin | ........................ | A61C 8/008 433/173 |
| 2014/0193775 A1* | 7/2014 | Hogan | ................. | A61C 8/0062 433/201.1 |
| 2014/0205970 A1* | 7/2014 | Courvoisier | ........... | A61C 8/005 433/174 |
| 2014/0377714 A1 | 12/2014 | Jahn | | |
| 2015/0164620 A1* | 6/2015 | Berger | ................. | A61C 8/0068 433/173 |
| 2015/0282907 A1* | 10/2015 | Zipprich | ................ | A61C 17/02 433/32 |
| 2017/0128176 A1* | 5/2017 | Vergoullis | ............ | A61C 8/0001 |

FOREIGN PATENT DOCUMENTS

| | | |
|---|---|---|
| DE | 202013005821 U1 | 7/2013 |
| EP | 2 829 250 A1 | 1/2015 |
| KR | 2013 0110850 A | 10/2013 |
| KR | 20130110850 A * | 10/2013 |
| WO | 2010108919 A2 | 9/2010 |

\* cited by examiner

SCAN ABUTMENT HAVING AN ENLARGED SCAN SURFACE

This application is a 371 of PCT/US2016/075795, filed, which claims foreign priority benefit under 35 U.S.C. § 119 of the German Patent Application No. 10 2015 118 285.8 filed Oct. 27, 2015, the disclosures of which are incorporated herein by reference.

The invention relates to a scan abutment for determination of the position of the plane of the front face (coronal) of a dental endosseous implant, wherein the abutment has a longish, hollow shaft and, apically, a base at the bottom side of the shaft, and the base with at least a part of its bottom side (apical) is attachable onto the front face (coronal) of the implant, wherein the base has a recess extending from its upper side to the bottom side of the base for receiving means for fixing the abutment on the implant, wherein the longish, hollow shaft has a side wall having at least one through hole and/or depression at its outer periphery, in particular in the form of an arch segment, wherein preferably the through hole or depression of the side wall extends from the bottom side of the shaft to the upper side of the shaft, thereby forming at least one planar surface in the plane between shaft and base. Particularly preferably, the planar surface is perpendicularly arranged to the central axis of the implant. Alternatively or additionally, the planar surface may preferably be parallely arranged to the plane of the bottom side of the base and/or the plane of the upper side of the shaft.

In dental prosthetics, CIM processes (computer-integrated manufacturing), such as CAD/CAM methods, increasingly gain in importance. Like this, it has meanwhile become customary in implant prosthetics to digitise the implant and residual tooth situation in the mouth of the patient and to design and manufacture the tooth replacement using CAD/CAM. So-called scan abutments are employed for digitization of the orientation of the implants by scanning a plaster model or the implants in the mouth of the patient.

Usually, scan abutments are cylinder-shaped devices made of a plastic, being screwed together with the implants with low fitting tolerance. These devices allow determining the three-dimensional position of the implants in the jaw via an optical scan with a table or intraoral scanner. The scan of the scan abutments thus serves for measuring as accurately as possible the position of the implants by scan of a plane parallely staggered in height of the upper side of the scan abutments and of the shaft of the scan abutment, of the position of the plane of the front face of the implant, as well as of the orientation of the implant. This works quite well for single implants being provided with one implant abutment and one crown.

For this purpose, the scan abutments of the state of the art have a longish shaft of a defined height to be able to determine the axis direction and x-y position of the implant in the jaw. Usually, the shaft is cylindrical. In the simplest design, the shafts are circular, but also other cross-sections are usual. In addition, e.g. also conical, wherein the largest diameter is implant-sided, and/or spherical geometries are known (e.g. CADstar).

In the case of so-called bridge constructions, where two or more implants are used as support for a prosthetic treatment, such as a dental bridge or a bar, the accuracy of the digitisation often is still not enough, because the occlusal plane of the implants must very accurately be determined for production of accurately fitting prosthetic treatments over a number of implants, because in bridge constructions the implants are connected to each other via the prosthetic treatment. In the case of inaccurate data of the occlusal plane, the prosthetic treatment manufactured lacks a precise fit. The required accuracy for determination of the position of the front face is not achieved in the case of known abutments, due to the large distance of the scanned plane at the upper shaft end of the abutment with respect to the coronal plane of the implant.

For this reason, up to now, the implant positions must be rescanned in the production based on the plaster model in the case of digitised production of the dental bridges supported by implants, and the coronal supporting surfaces (coronal planes of the implants) must be newly determined despite of available 3D-construction data. This rescanning is particularly time-consuming because the plaster model must be sent in together with the 3D-construction data from the dental laboratory to a central manufacturer. The central laboratory then rescans the dental model prior to the production of the bridges supported by implants and adjusts the digital data.

The height determination of the implant front face of the scan abutments mentioned below is made indirectly via determination of the height and orientation of the upper front face of the scan abutment.

The mentioned loss of accuracy has various causes. On the one hand, it is caused by the limited accuracy of the scanner and, on the other hand, by the tolerances on the part of the scan abutments. In particular, also accurate determination of the height position of the coronal implant front face(s) matters in the case of the aforementioned bridge constructions. Deviations of these height positons inevitably result in a non-accurately fitting attachable bridge, in the worst case the bridge has a freedom of movement, because the supporting surfaces of the implant bridges and the implant front faces in the 3D data set with respect to each other have not been accurately fitting.

It was an object of the invention, to develop scan abutments which reduce the mentioned disadvantages concerning the inaccuracies during scanning and at best avoid rescanning. In particular, it was the object to develop scan abutments enabling an improved data accuracy of the mesial, buccal, labial, oral and/or occlusal planes of the scan abutment(s) and thus of the coronal front face(s) and of the position of the implant(s).

The invention now provides a proposed solution as to how the tolerances of this height position within the scan abutment may be minimized as possible, namely by significantly reducing the distance of the planar-parallel plane of the coronal front face of the implant and of the surface(s) to be scanned of the scan abutment. The object is solved by a scan abutment according to claim 1, wherein advantageous embodiments are shown in detail in the subclaims as well as in the description.

Known scan abutments determine this height position of the respective implant front face(s) by a scan of the upper front face of the abutment attached to the respective implant. However, the coronal front face of the scan abutments is usually spaced approximately 10 mm or more from the front face of the implants. Therefore, the manufacturing tolerances of this geometry are correspondingly high for known scan abutments, since the measure extends over the whole length of the scan abutment, wherein it applies that "the longer a measure is, the more difficult is complying of a small tolerance".

It is the core of the invention to minimize as possible the distance and thereby the tolerances of the scan abutment and the scan between implant front face and the surface of the scan abutment being measured for the height position during scanning (measure "X" in drawing).

According to the invention, a reference edge, presently referred to as surface(s) 6 and 7, is provided, which does no longer lie on the coronal front face of the scan abutment, synonymously to the upper side of the shaft of the scan abutment, at a distance of about 10 to 15 mm to the coronal front face of the implant, but preferably at a distance of still 1 to 3 mm. In doing so, the tolerances may be reduced by about approx. 50%. This improvement of the tolerance corresponds to an improvement of the tolerance of approximately 20 to 30 μm (micrometers) such that improvement of the scan accuracy is achieved. Like this, DIN ISO 2768-1 specifies general tolerances—fine from 2 +/− 0.05 mm up to 10 +/− 0.1 mm. ISO 286 specifies a tolerance system for measures of length of plastic parts of category A according to tolerance series 9 and measures of 1 to 3 mm from 0.025 mm and for measures of 10 to 18 mm from 0.043 mm.

The scan abutment according to the invention is material-integral, i.e. an integral scan abutment, i.e. scan abutment made from one piece of material.

However, the whole available diameter is required for the shaft of the scan abutment due to the low diameters of implants, which are usually between 3.3 and 6.0 mm. Consequently, the whole surface for height determination automatically fell on the upper front face of the scan abutment, synonymously upper side of the shaft. However, the upper front race of the abutment is furthest spaced from the front face of the implant. In order now to obtain a parallel surface to the front face of the implant having smallest possible distance, e.g. 2 mm, it is proposed according to the invention to discontinue the shaft, preferably by 90° of its periphery in an alternative. This through hole of the shaft may be formed greater or less than 90°, in particular in the form of an arch segment. If a through hole having an opening angle of less than <90° is chosen, the surface formed has not the most optimal size and is may happen that the surface may not be measured with the desired accuracy. If an opening angle of the through hole of greater than >120° is chosen, the scan accuracy of the shaft decreases. Balance and increase of the scan accuracy of the parallel surfaces being formed by the through hole and the upper side of the shaft of the scan abutment is achieved with an opening angle of approximately 90° to less than or equal to 120° (each +/−10°, in particular +/−5°).

Alternatively or additionally, in the case of scan abutments for larger implant diameters from approximately 4.5 mm an increment of the lower region of the shaft to the base may be made, whereby a further surface, in particular a circumferential further surface occurs. This surface can serve for increase of the planar-parallel total surface (surfaces 6+7), in turn preferably being planar-parallely arranged to the coronal implant front face. This enlarged surface can be measured still better and more accurately by the scanner. Preferably, the remaining upper side of the shaft, which preferably also is parallely arranged to the surfaces according to the invention of the scan abutment, is additionally scanned in the scanning procedure in all embodiments of the invention.

In order to take advantage of this geometry, the scanner and the algorithm of the related software for measuring the new at least one surface were adjusted such that during orientation of the scan with the CAD scan abutment libraries they consider the at least one new surface being closest to the implant front face. The software 3shape is used for the scan of the scan abutment according to the invention, wherein other systems may also be adjusted correspondingly.

Thus, a subject matter of the invention is a scan abutment for determination of the position (x,y,z-coordinates) of the front face of a dental endosseous implant, in particular in the jaw of a patient or as laboratory analogue in a model, wherein the abutment has a longish, hollow shaft and a base on the bottom side of the shaft, and the base with at least a part of its bottom side is attachable onto the front face of the implant, wherein the base has a recess extending from its upper side to the bottom side of the base, in particular for receiving of means for fastening the abutment on the implant, wherein the longish, hollow shaft is formed from a side wall, and the side wall at least in part in the region directly above the base has at least one through hole and/or depression at its outer periphery in the side wall, in particular in the direction toward the longitudinal axis of the shaft, thereby forming at least one planar surface in the plane between shaft and base by the through hole and/or the depression, in particular the planar surface forms on the upper side of the base. Preferably, the plane may be perpendicularly arranged to the central axis of the implant. In addition, it is particularly preferred for the central axis of the scan abutment and the central axis of the implant to be able to be coaxially arranged. Further through holes may result in planar surfaces which may be parallely staggered to the first surface and/or horizontally lie on the periphery of the side wall. Likewise, it may alternatively be preferred for the surfaces to be parallely arranged to the plane of the bottom side of the base and/or the plane of the upper side of the shaft.

A through hole is considered as continuous recess, thus a hole, in the side wall, extending from the outer surface of the side wall until the inner surface of the side wall of the hollow shaft. A depression in the side wall of the shaft does not comprise a shaft in the form of a cone section with planar side wall. A depression comprises at least one undercut in the side wall of the shaft which extends from the outer surface of the shaft into the side wall, but is not formed until the inner surface of the side wall.

Preferably, the bottom side of the base may be attached accurately fitting onto the front face of the implant. For this purpose, the base in particular has a connection geometry being formed appropriately to the connection geometry of the respective present implant. The means for fixing the abutment on the implant may comprise screws, nails, bolts or further means sufficiently known by the person skilled in the art for fastening abutments on implants.

The respective planes according to the invention are understood to mean those geometric planes which may be laid, for example, into the respective surfaces, front faces, uppers sides or bottom sides, such as, in particular, the plane between shaft and base, as respectively one plane may be laid into the surface of the shaft or between the bottom side of the shaft and the upper side of the base, or into the front face of the implant.

The longish, hollow shaft is formed by the side wall forming the outer boundary of the shaft, wherein the hollow shaft has an inner lumen extending along the longitudinal axis. In particular, the side wall is cylindrical, and may be discontinued according to the invention and/or have a lower diameter than the base.

According to the invention, the longish shaft has horizontal and/or vertical, planar through holes and/or depressions, all preferably being planar-parallely formed to the at least one surface and, optionally, the further surface. According to a further alternative, the shaft may have vertical, linear through holes and/or depressions or vertical, planar surfaces to further improve the scan accuracy in the trajectory of the implant front face.

Moreover, the shaft (without base) has a defined height (Y) of 5 mm to 20 mm, in particular of 5 to 15 mm, preferably about 8 to 13 mm, in particular with a tolerance of plus/minus 0.05 mm, preferably to plus/minus 0.02 mm. Thus, the scan data are improved with respect to the fault tolerance by approximately 20 to 50% despite of the low total height (shaft height Y and base height X) of 9 mm to 15 mm. This improvement corresponds to a height accuracy of approximately 20-30 μm (micrometers).

According to the invention, the height (X) of the base preferably amounts to greater than or equal to 0.1 to 10 mm, in particular from 0.75 mm to 5 mm, preferably about 1 to 3 mm, in particular with a tolerance of plus/minus 0.1 mm, preferably to plus/minus 0.02 mm, preferably to plus/minus 0.005 mm.

A preferred ratio of height X to height Y amounts to 1:1.5 to 1:20. Preferably, the ration is in the range of 1:5 to 1:13.

According to a further preferred embodiment of the invention, the side wall of the longish, hollow shaft, has at least one through hole at least in part along a longitudinal side of the shaft. In particular, the at least one through hole amounts from 5% to 100% of the height of a longitudinal side of the shaft, preferably from 10% to 100%, preferably 10% to 90%, 20% to 80% or 20 to 70%. Preferably, greater than or equal to two through holes, in particular from 2 to 10, 2 to 5 or 2 to 3, may also be arranged in the side wall along a longitudinal side which may then be arranged vertically or staggeredly one above the other. Alternatively, at least two through holes horizontally spaced from each other may be provided at the outer periphery of the side wall, which respectively extends at least in part along a longitudinal side of the shaft, the horizontally spaced through holes may, for example, be spaced from each other in an angle of 2° to 330°, such as, for example, from 5° to 90°. Preferably, each through hole has, respectively independently, a height of at least 10% to 100% of the height of the shaft, preferably 15% to 100%, 20 to 80% or 10 to 30%. Preferably, greater than or equal to two to 10 through holes, in particular 2 to 10, 2 to 5, 2 to 3, are arranged in the side wall along a longitudinal side which preferably amounts respectively 10% to 30% of the height of a longitudinal side of the shaft.

Figures 3, 3A, 3B, 3C, 3D:
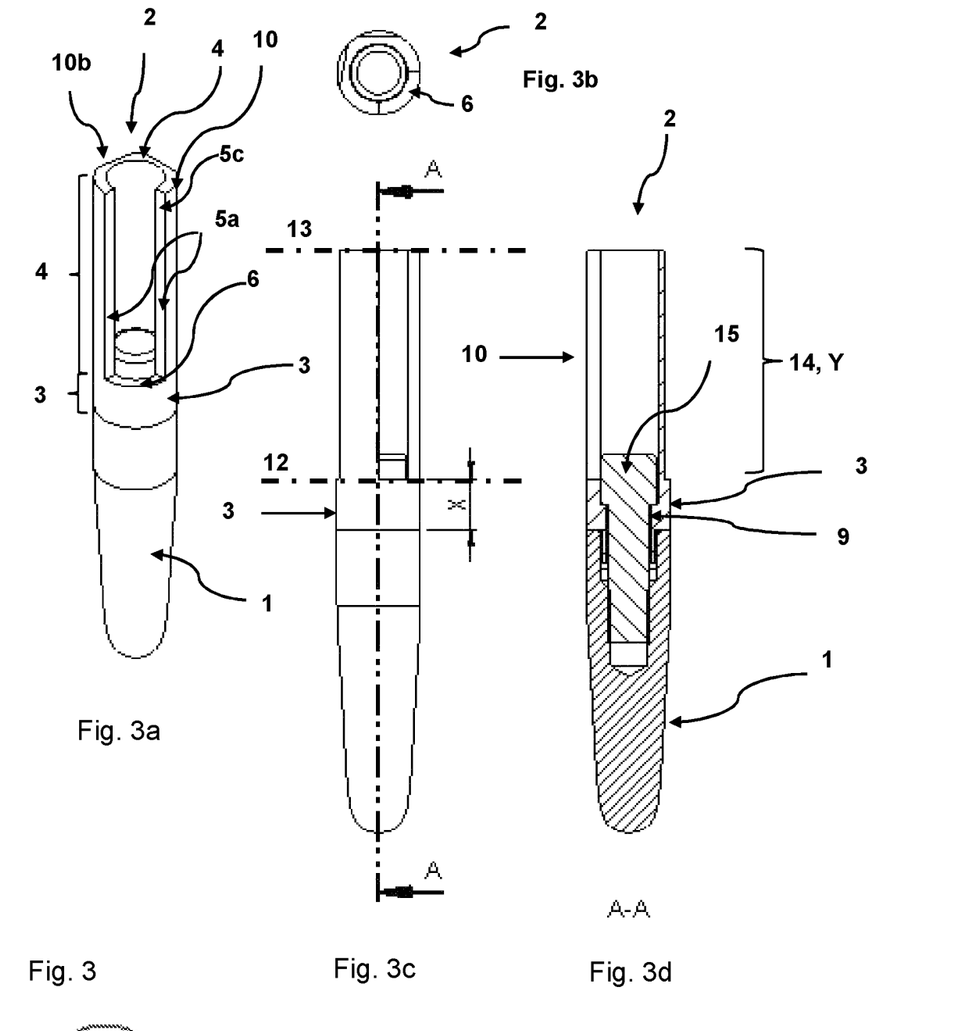
FIG. 3a: perspective view of the scan abutment 2 with implant 1.
FIG. 3b: axial cross section of the scan abutment 2.
FIG. 3c: lateral view of the plane A.
FIG. 3d: longitudinal cross-section.

A through hole in the form of an arch segment having an opening angle (alpha, α) of 80° to 130°, preferably of approximately 90° to 120°, as shown in FIGS. 2 and 3, is preferred. According to a further alternative, the side wall has a plurality of surfaces vertically arranged in the height planar-parallely with respect to each other, in particular in the form of vertical arch segments planar-parallely arranged one above the other, preferably having an aforementioned opening angle.

Figure 5A:
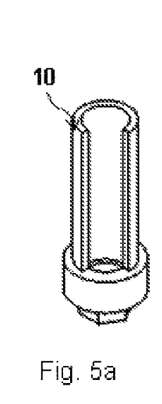
FIG. 5a-c: alternative embodiments of the scan abutments with circular outer shaft (FIG. 5a), with elliptical outer shaft (FIG. 5b), with quadrangular outer shaft (FIG. 5c)
Figure 5B:
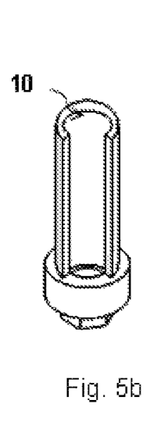

According to alternative embodiments, the side wall of the shaft may thus have a plurality of through holes. In this case, the through holes may also represent rectangular or squaric recesses (FIG. 5a, 5b). A plurality of through holes, for example, horizontal, lamellar through holes or vertical, lamellar through holes may be formed in the side wall for maximal improvement of the scan resolution such that the side wall of the shaft, for example, is grid-shapely formed.

Moreover, the subject matter of the invention comprises a scan abutment, whose side wall of the longish, hollow shaft has at least one through hole on a longitudinal side of the shaft having an opening angle of 5° to 330°, in particular in the outer periphery of the side wall, measured from a longitudinal axis of the shaft. Preferably, the side wall has a through hole having an opening angle greater than or equal to 10 to 120°, in particular from 30° to 120°, preferably of 90° of plus/minus 20°, preferably of plus/minus 10°, plus/minus 5°. According to particularly preferred alternatives, the side wall has at least one through hole having an opening angle of greater than or equal to 90° to 120°, preferably of 100° with plus/minus 15°, preferably plus/minus 10°, particularly preferably of plus/minus 5°. According to a further preferred alternative, the side wall of the longish, hollow shaft has at least one through hole on a longitudinal side of the shaft having an opening angle of 90°, in particular with plus/minus 30°, wherein the opening angle of the through hole is measured starting from the longitudinal axis in the direction of the outer periphery of the side wall. The through hole may extend the whole length of the shaft or a part of the shaft.

According to a further embodiment of the invention, the at least one through hole of the side wall and/or the depression at the outer periphery of the side wall of the shaft extends from the bottom side of the shaft to the upper side of the shaft.

Figure 4:
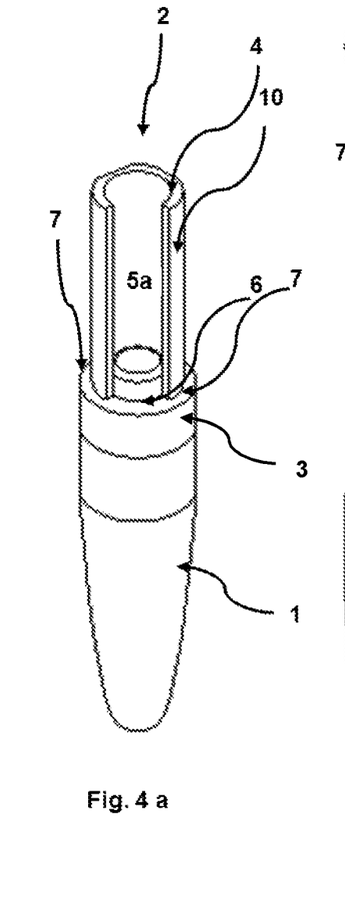
FIG. 4a: perspective view of the scan abutment 2 with implant 1.
FIG. 4b: axial cross-section of the scan abutment 2.
FIG. 4c: lateral view of the plane A.
FIG. 4d: longitudinal cross-section.
Figure 6A:
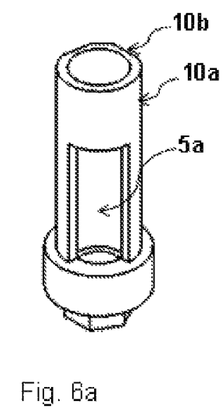
FIG. 6a-c: alternative scan abutments with through holes 5a along a longitudinal axis of the shaft (FIGS. 6a and 6b: opening angle alpha=90°)
Figure 6B:
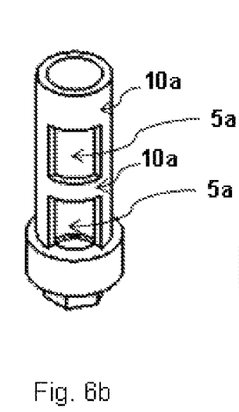
Figure 8A:
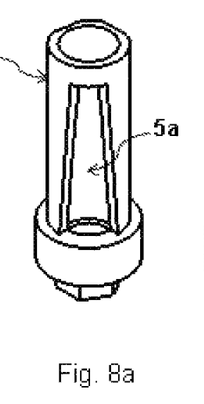
FIGS. 8a and 8b: scan abutments with a through hole 5a of the side wall at the outer periphery.
Figure 8B:
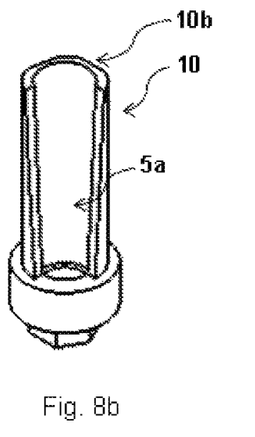

Moreover, the following alternatives may be realised, in which the side wall of the shaft, at its outer periphery, a) has at least one through hole in the form of an arch segment, circle segment, segment of an ellipsis or of a triangle, in particular in the plane of a cross-section of the scan abutment, i.e. in the top view starting from a longitudinal axis as reference point, as shown in FIGS. 3a, 3b and 4b, or b) has at least one through hole in the form of a quadrangle, such as rectangle, square, or trapezoid, in the outer periphery of the side all, as shown in FIGS. 8a and 8b, in particular the at least one though hole in a) and/or b) in the side wall of the shaft extends from the bottom side of the shaft to the upper side of the shaft, preferably the height of the through hole corresponds to at least 10% of the height of the shaft or c) at least one depression exists in the form of an arch segment, circle segment, segment of an ellipsis or in the form of an U- or V-shaped groove, U- or V-shaped channel, as shown in FIGS. 6a and 6b, or in the form of a hollow cylinder, in particular the at least one surface is thereby formed in a aforementioned form. Preferably, the depression may exist as groove or channel restricted by at least two side walls and a wall laying in between with preferably orthogonal U-shaped arrangement. Alternatively, two side walls may V-shapely exist in an acute angle.

According to a further particularly preferred embodiment of the invention, a scan abutment may have a shaft in which at least one outer diameter of the longish shaft is smaller than one of the outer diameters of the base, wherein at least one further planar surface is formed in the plane between shaft and base such that a planar total surface preferably forms as the sum of the one planar surface and the further planar surface. Preferably, the planar surface is arranged at a right angle to the axis of the implant. The further planar surface preferably is planar-parallel to the at least one surface.

Particularly preferably, the outer diameter of the longish shaft is smaller than the outer diameter of the base, wherein at least one further planar surface forms in the plane between shaft and base, which is part of a planar total surface in a plane as the sum of the one planar surface and the further planar surface.

The scan abutments according to the invention preferably has at least one surface(s) and at least one further surface being planar-parallely arranged with respect to each other in one plane. Preferably, the side wall of the shaft is flattened in one, two, three to eight regions, preferably the side wall is planar. Preferably, the side wall is planar in these regions from the upper side of the base to the bottom side of the shaft.

According to a particularly preferred embodiment, in particular in the case of scan abutments having a larger diameter, the at least one outer diameter of the longish shaft may be smaller than the outer diameter of the base or one of the outer diameters of the base, wherein at least one further planar surface, preferably circumferenting around the shaft, is formed in the plane between shaft and base. This may be the case, for example, for elliptical or rectangular shaft geometries. Preferably, this surface is perpendicularly arranged to the central axis of the implant. In alternatives, is may be planar-parallely arranged to the plane of the bottom side of the base and/or the plane of the upper side of the shaft and, in particular, planar-parallely to the at least one surface.

According to a further alternative, the thickness ($d_2$) of the side wall of the shaft at the outer periphery of the shaft may vary, in particular the outer periphery of the sidewall has at least two diameters as, for example, in the case of ellipses. For example, two enlarged further surface may be formed in the case of an elliptical outer periphery of the shaft along the longitudinal axis. Therefore, an embodiment, in which the outer periphery of the side wall of the hollow shaft is at least in part elliptical along the longitudinal axis as, for example, in the case of a shaft in the form of an elliptical cylinder, is particularly preferred.

An outer periphery of the longish shaft is considered as each diameter of the longish shaft. Preferably, an outer diameter of the shaft is understood to means the greatest outer diameter of the longish shaft.

According to a further preferred embodiment of the invention, the at least one planar surface and the one further planar surface form the surface of the base for improving the scan accuracy. Preferably, both surfaces are perpendicularly arranged or in the normal, respectively, to the central axis of the implant. In this case, the axis of the scan abutment and of the implant are coaxially arranged at the same time.

Figure 5C:
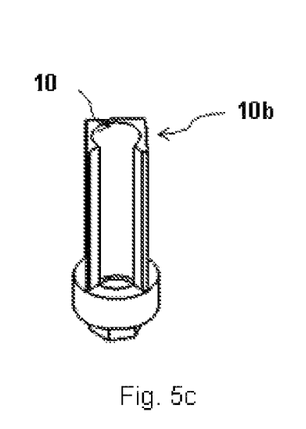

In the case of preferred scan abutments, the side wall of the shaft may have the form of a a) cylinder, in particular of a hollow cylinder, prism, such as, for example, having rectangular or squaric, as shown in FIG. 5c, upper and bottom side, preferably having rectangular or squaric cross-section, and preferably with rounded vertical edges, preferably a right prism having almost rectangular cross-section with rounded edges; or b) the side wall has the form of a cone, or c) ellipsoid (FIG. 5b), d) polyhedron, in particular of a regular and convex polyhedron, preferably of an octahedron or icosahedron, or of a e) sphere, wherein in a), b) or c) the side wall of the shaft has at least one through hole and/or depression at least at its outer periphery, in particular along a longitudinal axis of the shaft, thereby forming at least one planar surface in the plane between shaft and base by the through hole and/or the depression, in particular the planar surface forms on the upper side of the base. Preferably, the surface may be parallely arranged to the plane of the bottom side of the base and/or the plane of the upper side of the shaft. According to further preferred alternatives, the outer surface of the side wall of the scan abutment may additionally be at least in part flattened or planar, respectively.

In the case of particularly preferred scan abutment, the side wall of the shaft may have the form of a cylinder, in particular of a right prism, preferably having the base area of a quadrangle or pentagon with an edge length of the base area of 3.5 mm to 6.5 mm, particularly preferably having an almost rectangular cross-section. In this case, it is particularly preferred for the right prism, in particular having a rectangular, preferably having a squaric cross-section, to have rounded edges in the height of the prism. The radius of the edges preferably amounts from 0.1 to 1 mm.

According to a further preferred alternative, the base of the scan abutment may exist in the form of a truncated cone, wherein the base of the truncated cone preferably forms the planar upper surface of the base and, in particular, the top surface of the truncated cone forms the bottom side of the base. Appropriately, the planar top surface may form the planar upper side of the base.

In a particularly preferred embodiment of the invention, the depth (=curve radius, $r_B$) of the surface in the plane, measured from the outer periphery ($M_1$=barrel) of the side wall to the longitudinal axis of the shaft, may be from greater than to equal to 0.2 to 4 mm, in particular from 0.25 to 0.8 mm, preferably from 0.3 to 0.8 mm, particularly preferably from 0.4 to 0.7 mm.

According to a further particularly preferred embodiment of the invention, the at least one depth ($d_1$) of the further surface in the plane, measured from the outer periphery ($M_2$) of the base to the outer periphery ($M_1$) of the shaft, may be from greater than to equal to 0.2 to 4 mm, in particular from 0.25 to 1.5 mm, preferably from 0.3 to 0.8 mm, particularly preferably from 0.4 to 0.7 mm. FIGS. 5 to 10 show such an embodiment.

Preferably, the scan abutments according to the invention have as the at least one surface(s) 6 and at least one further surface 7, which are plane-parallely arranged with respect to each other, in the sum a surface(s) at least of 1 mm$^2$ to 25 mm$^2$, preferably of 5 to 20 mm$^2$, particularly preferably of 7 to 15 mm$^2$, 7 to 20 mm$^2$ or 7 to 25 mm$^2$ are alternatively preferred.

In addition, it may be preferred for the surfaces of the scan abutment to be provided at least in part with a rough surface structure, preferably the at least one surface and the further surface as well as, optionally, the outer surface of the side wall and, optionally, the upper side of the shaft may be provided with a rough surface structure. Powder coating, sandblasting, etching etc. are suitable for changing the surface, without limiting the methods to these methods.

The material of the scan abutments according to the invention may be selected from a polymeric material, filled polymeric material, metal, an alloy, such as titanium, cobalt chrome, gold, a fiber-reinforced polymer, an alloy, hybrid material, wherein the polymeric material may be selected from fluoropolymers, polysulfide-containing polymers, polysulfone-containing polymers, polyaryletherketones, polyimides, PC (polycarbonate), PAEK (polyaryletherketones), PEEK (polyetheretherketones), PEK (polyetherketones), PEKK (poly(etherketoneketones)), PEEEK (poly(etherether-etherketones)), PEEKK (poly(etheretherketoneketones)), PEKEKK (poly(etherketone-etherketoneketones), PES (polyarylsulfones), PPSU (polyarylsulfones), PSU (polysulfones), PPS (polyphenylene sulfides), PFA (perfluoroalkoxy polymers), PFE (poly(fluorenylene ethynylene) polymers), PVDF (polyvinylidene fluorides), PCTFE (polytetrafluoroethylenes), PAI (polyamide imides), PI (polyimides), PEI (polyetherimides), PBI (polybenzimidazoles). Cobalt chrome, titanium, gold etc. are preferred as metallic alloy or metal.

A further subject matter of the invention is the use of a scan abutment, wherein the one surface and/or the at least one further surface a) are perpendicularly arranged to the central axis of the implant when the scan abutment with its bottom side of the base is attached onto the front face of the implant for determination of the position (x,y,z-coordinates) of the front face of a dental endosseous implant, or b) the central axis of the scan abutment is coaxially arranged to the central axis of the implant, and the one planar surface and/or the at least one further surface is perpendicularly arranged to the central axis of the implant.

The through holes and/or depressions according to the invention forming the first surface and, optionally, the further surfaces may independently be used for all shaft geometries and materials appearing reasonable for the person skilled in the art, regardless of the above statements.

The invention is clarified based in the figures without limiting the invention to these exemplary embodiments.

The figures show: FIG. 2a-e: scan abutment according to the invention without implant with implant screw for middle to large diameters, for example 4.5 mm, FIG. 3a-e: scan abutment 2 according to the invention for small diameters, for example 3.3 mm, FIG. 4a-d: scan abutment according to the invention for middle to large diameters, for example 4.5 mm, FIGS. 7a and 7b: Scanabutment with two horizontally spaced through holes 5a.

Figures 1, 2A, 2B, 2C, 2D, 2E:
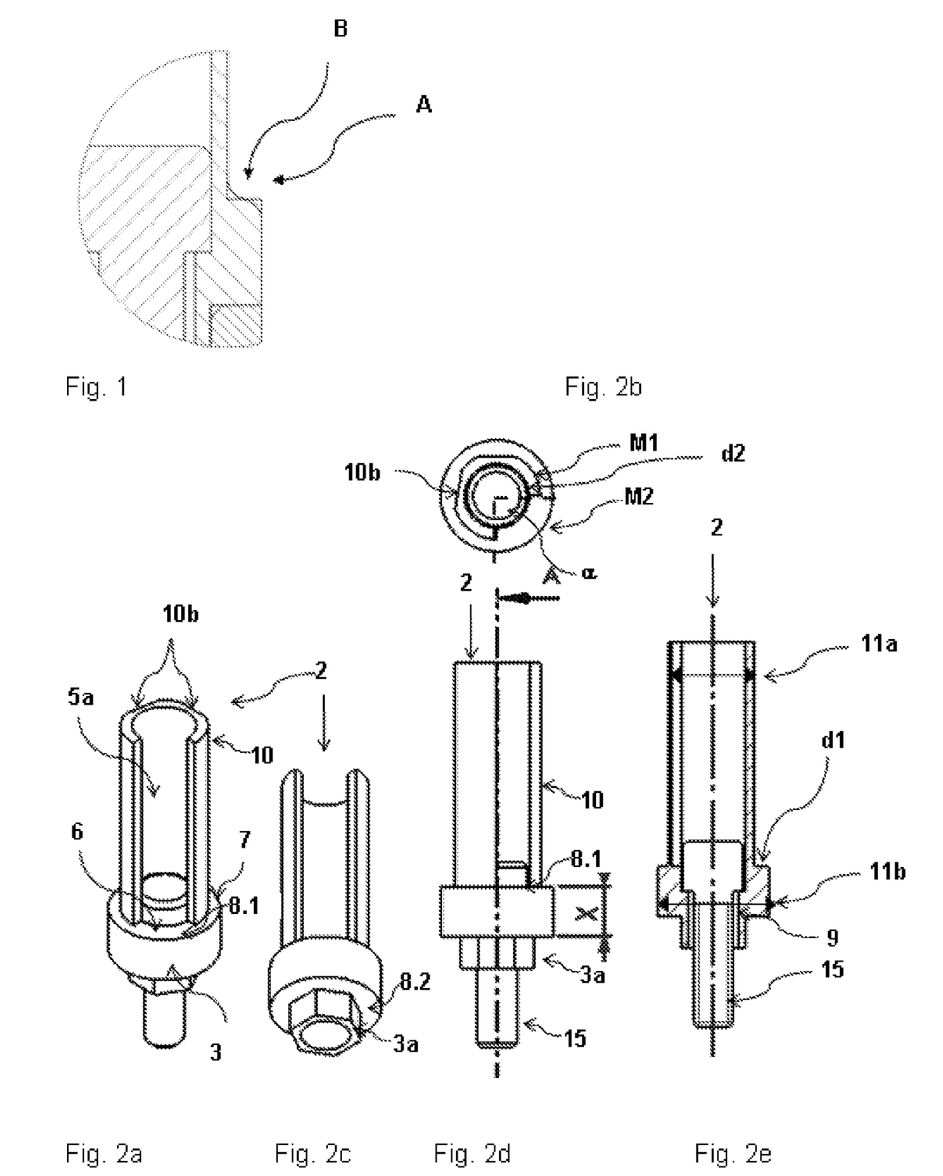
FIG. 1: measuring of small surfaces A by a scanner, being roundedly measured by the scanner according to B.
FIG. 2a: perspective view of the scan abutment 2 with implant 1.
FIG. 2b: axial cross-section of the scan abutment 2.
FIG. 2c: view of the scan abutment from an angle below.
FIG. 2d: lateral view of the plane A.
FIG. 2e: longitudinal cross-section.
Figure 3E:
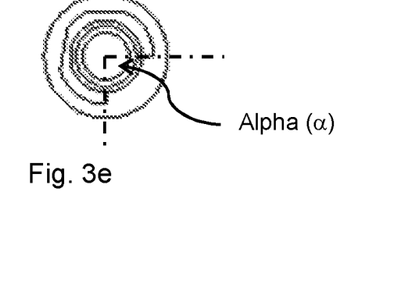
FIG. 3e: opening angle alpha (α) 90° of the through hole.

FIG. 1 shows the too small surface B being measured with rounded edges A by a scanner. FIGS. 2a to 2e show a scan abutment 2 according to the invention without implant 1 with fastening means 15. The scan abutment 2 of FIG. 2a has a through hole 5a in the side wall 10 having an opening angle α of 90° (FIG. 2b). The outer surface of the side wall 10 of the scan abutment 2 may additionally be flattened or planar 10b, respectively, such that further planar surfaces form on the outer surface of the shaft 4. FIG. 2a-c the planar upper side 8.1 and the planar bottom side 8.2 of the base as well as the hexagon socket-connection geometry 3a. FIG. 2d show a view in the plane A in which the height X of the base 3 is shown. FIG. 2e shows an outer diameter 11a of the longish shaft and the diameter 11b of the base 3. FIG. 2b shows the outer periphery $M_1$ of the barrel of the side wall 10 with flattened side wall 10b, as well as the outer periphery $M_2$ of the base 3. $d_1$ corresponds to the depth of the surface 7, corresponding to the difference of 11b and 11a. $d_2$ corresponds to the thickness of the side wall 10, the depth of the arch segment 6+7 may thus have a depth of $d_1+d_2$. Alpha (α) is the opening angle. FIGS. 3a to 3e show a scan abutment 2 according to the invention for small diameters of, for example 3.3 mm. In the perspective view of FIG. 3a, the scan abutment 2 has a planar, parallel surface 6 in the through hole 5a, laying in the upper plane 12 of the base 3 (FIG. 3b). Preferably, the edge(s) 5c of the through hole are orthogonal to the side wall 10. The scan abutment has a base 3, in particular having a (FIG. 2c, 2d) connection geometry 3a, in particular a hexagon or octagon socket outer profile, for fastening the abutment on the front face of an implant 1. The connection geometry is not visible. The shaft 4, with upper side of the shaft 4.1 or upper front face, respectively, and bottom side 4.2 of the scan abutment 2 is provided with a through hole 5a in the side wall 10 in which the planar, parallel surface 6, see FIGS. 3a and 3b, is formed in the upper plane 12 of the base 3. The plane 12 is shown in FIG. 3c as section plane between bottom side 4.2 of the shaft and upper side 8.1 of the base 3, or the upper plane 13 on the upper side 4.1 of the shaft or the upper front face of the scan abutment 2, respectively. FIG. 3d shows a fastening means 15, such as screw, bolt, in the scan abutment 2 as well as the longitudinal side 14 of the shaft and its height Y. The recess 9 in the base 3 may be in the form of a hole or a thread for passing through, for example, a screw or a bolt. The opening angle alpha here 90° is shown in FIG. 3e.

In FIGS. 4a to 4d, scan abutments according to the invention for middle to large diameters, for example 4.5 mm, are shown. Like this, the perspective view of the scan abutment 2 having shaft 4 and side wall 10 on an implant 1 of FIG. 4a shows a through hole 5a as well as the planar surface 6 and the planar, parallel surface 7, forming by at least one outer diameter 11a of the longish shaft 4 being smaller than one of the outer diameters 11b of the base 3. The total surface 6+7 lies the upper plane 12 of the base 3 and is particularly large especially in the region of the arch segment in which 6+7 are laying. FIG. 4b shows a top view on the scan abutment 2 on the upper side 4.1 of the shaft as well as the upper side of the side wall 10 with surface 6 and surface 7. The height X of the base 3, the height Y of the shaft as well as the longitudinal side 14 of the shaft 3 of the scan abutments 2 are shown in FIGS. 4c and 4d. The bottom side 8.2 of the base (s. also FIG. 2c) is arranged on the front face of the implant 1.1.

FIGS. 5a to 5c show alternative shaft geometries. FIG. 5a shows a circular outer shaft having a through hole 5a, FIG. 5b shows an elliptical shaft having a through hole, and FIG. 5c shows a quadrangular shaft. The opening angle respectively amounts to approximately 90°.

Figure 6C:
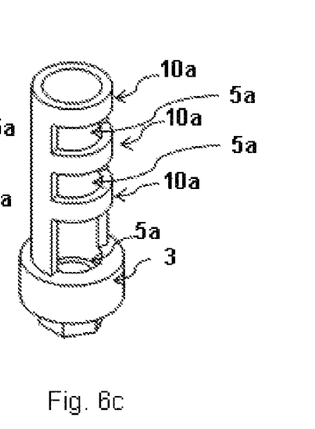

FIGS. 6a-c show alternative scan abutments having one to three through holes 5a being vertically distributed in the height along a longitudinal axis of the shaft. The opening angle in FIG. 6a amounts to alpha=90°, in FIG. 6b the other the opening angle alpha in the two through holes, vertically arranged one above, also amounts to respectively 90°. Three through holes, vertically arranged one above the other, respectively having an opening angle alpha of 150° with additional circumferential surface 7 are shown in FIG. 6c.

Figures 7A, 7B:
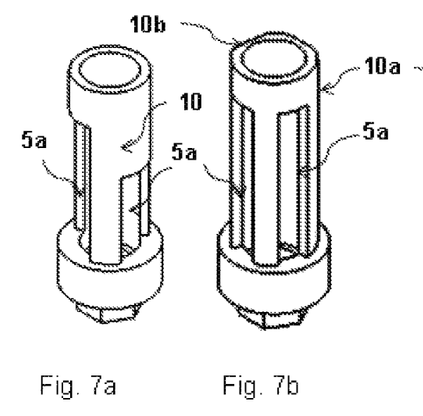
Figures 9A, 9B:
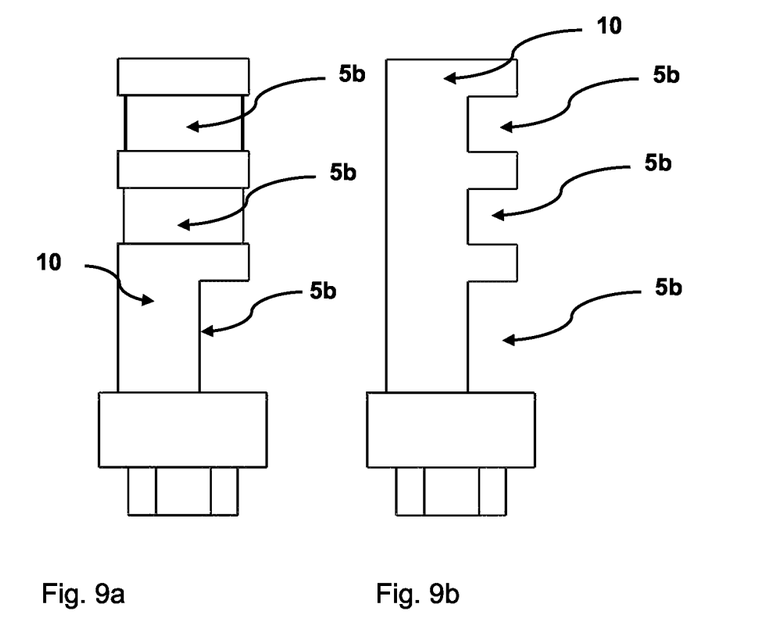
FIGS. 9a and 9b: scan abutment 2 with U-shaped depressions 5b.
Figures 10A, 10B:
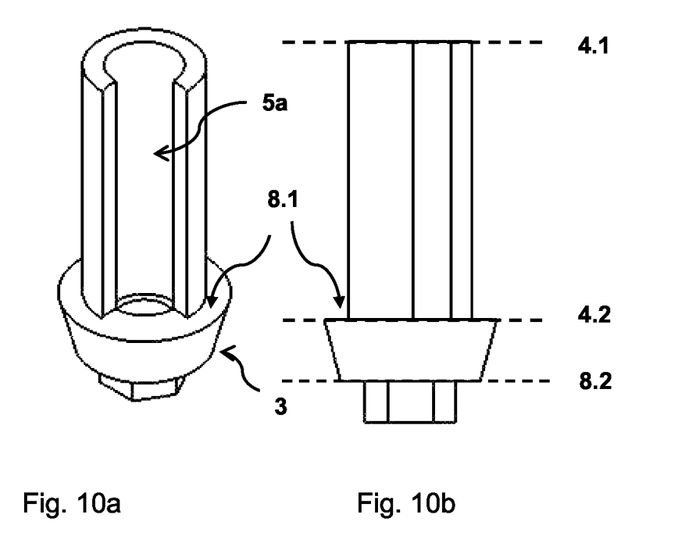
FIGS. 10a and 10b: scan abutment 2 with a truncated cone-like base 3.

The scan abutments of the FIGS. 7a and 7b have two horizontally spaced through holes 5a in the form of a rectangler at the outer periphery of the side wall 10, wherein the side wall remains circumferential 10a in the upper region of the shaft. FIGS. 8a and 8b show scan abutments having a through hole 5a of the side wall at the outer periphery in the form of a quadrangle, here of a trapezoid 5a, wherein a circumferential side wall 10a continuously exists in FIG. 8a. The trapezoid-shaped through hole 5a in FIG. 8b extends from the bottom side of the shaft 4.2 to the upper side 4.1 of the shaft. In FIGS. 9a and 9b, scan abutments 2 having U-shaped depressions 5b, forming further planar, parallel surfaces 6 along the longitudinal axis of the scan abutment, are shown, which are staggered in height. FIGS. 10a and 10b show a scan abutment 2 having a quadrangular through hole 5a, extending from the bottom side of the shaft 4.2 to the upper side 4.1 of the shaft, and having a truncated cone-like base 3, wherein the planar base area of the truncated cone forms the upper side 8.1 of the base. Moreover, FIGS. 10a and 10b show the enlarge upper side 8.1 and thus the enlarge further surface 7, being formed by the planar base area of the truncated cone. 8.1 shows the planar upper side of the base 3 and 8.2 shown the planar bottom side of the base.

REFERENCE SIGNS 1 implant, front face (1.1) of the implant (1)
2 scan abutment
3 base, in particular with connection geometry for fastening the abutment at the front face of an implant, 3a connection geometry, in particular hexagon or octagon outside geometry
4 shaft, with upper side of the shaft (4.1) or upper front face, respectively, and bottom side (4.2) of the shaft
5a through hole/discontinuity,
5b depression
5c edge
6 planar, parallel surface in through hole or depression in the upper plane (12) of the base (3),
7 planar, parallel surface (7) forming by at least one outer diameter (11a) of the longish shaft (4) being smaller than one of the outer diameters (11b) of the base (3), in particular in the upper plane (12) of the base (3),
8.1 upper side of the base (6+7); or 8.1 upper surface of the base, respectively
8.2 bottom side of the base, or 8.2 bottom surface of the base, respectively
9 recess in the base, in particular hole or thread for passing through, for example, a screw
10 side wall forming a shaft or side wall of the shaft, respectively, 10a circumferential side wall, 10b flattened or planar side wall, respectively,
11a an outer diameter of the longish shaft
11b outer diameter of the base
12 plane (12) is section plane between bottom side (4.2) of the shaft and upper side (8.1) of the base (3), or
13 upper plane on the upper side (4.1) of the shaft or upper front face, respectively
14 longitudinal side of the shaft
15 fastening means, such as screw, bolt
X=height base, Y=height shaft; $M_1$=outer periphery ($M_1$=barrel) of the side wall (10); $M_2$=outer periphery ($M_2$) of the base (3), $d_1$=depth=difference of 11b and 11a, $d_2$=thickness of the side wall (10), opening angle (alpha, α)

The invention claimed is:

1. Scan abutment (2) for determination of the position (x,y,z-coordinates) of a front face (1.1) of a dental endosseous implant (1), wherein the abutment (2) has a longish, hollow shaft (4) and a base (3) at the bottom side (4.2) of the shaft (4), and the base (3) with at least a part of its bottom side (8.2) is attachable onto the front face (1.1) of the implant (1), wherein the base (3) has a recess (9) extending from its upper side (8.1) to the bottom side (8.2) of the base (3), wherein
the shaft (4) is formed from a side wall (10), wherein the side wall (10) at least in part in the region directly above the base (3) has at least one through hole (5a) and/or depression (5b) at its outer periphery in the side wall (10), thereby forming at least one planar surface (6) in the plane (12) on the upper side of the base between shaft (4) and base (3) by the through hole (5a) and/or the depression (5b), wherein at least one outer diameter (11a) of the shaft (4) is smaller than one of the outer diameters (11b) of the base (3), wherein at least one further planar surface (7) circumferenting the shaft (4) at least in part is formed in the plane (12) between shaft (4) and base (3), wherein the one further planar surface (7) is planar-parallel to the at least one planar surface (6).

2. Scan abutment according to claim 1, wherein
a) the at least one through hole (5a) is positioned at least in part along a longitudinal side (14) of the shaft (4), and/or
b) at least two through holes (5a) are positioned at its outer periphery being horizontally spaced from one another, each extending at least in part along a longitudinal side (14) of the shaft (4).

3. Scan abutment according to claim 1, wherein the at least one through hole (5a) along a longitudinal side (14) of the shaft (4) has an opening angle of 5° to 330° in the outer periphery of the side wall, measured from a longitudinal axis of the shaft (4).

4. Scan abutment according to claim 3, wherein
the at least one through hole (5a) at a longitudinal side of the shaft (4) has an opening angle of 90°, plus/minus 30° in the outer periphery of the side wall, measured from a longitudinal axis of the shaft (4).

5. Scan abutment according to claim 1, wherein
the through hole (5a) of the side wall (10) and/or the depression (5b) at the side wall (10) of the shaft (4) extend from the bottom side (4.2) of the shaft (4) to an upper side (4.1) of the shaft (4).

6. Scan abutment according to claim 1, wherein
a) the at least one through hole (5a) and/or depression (5b) at the outer periphery in the side wall (10) form at least one planar surface (6) in the plane (12) on the upper side of the base in the form of an arch segment, circle segment, segment of an ellipsis or of a triangle, or
b) the at least one through hole (5a) has the form of a quadrangle in the outer periphery of the side wall, or
c) the at least one depression (5b) exists in the form of an U- or V-shaped groove, U- or V-shaped channel or in the form of a hollow cylinder.

7. Scan abutment according to claim 6, wherein the at least one through hole (5a) has the form of a rectangle, square, or trapezoid.

8. Scan abutment according to claim 1, wherein
the base (3) exists in the form of a truncated cone.

9. Scan abutment according to claim 1, wherein
a height (X) of the base is 0.1 to 10 mm with a tolerance of plus/minus 0.02 mm.

10. Scan according to claim 1, wherein
the side wall (10) of the shaft (4) exhibits the form of a) a cylinder, b) a cone, c) ellipsoid, d) polyhedron, or e) a sphere, and wherein the surface (6) is arranged parallel to the plane of the bottom side (8.2) of the base (3) and/or the plane of the upper side (4.1) of the shaft (4).

11. Scan abutment according to claim 1, wherein
a depth of the surface (6) in the plane (12), measured from the outer periphery ($M_1$) of the side wall (10) to the longitudinal axis of the shaft (4), is from greater than to equal to 0.2 to 4 mm.

12. Scan abutment according to claim 1, wherein
at least one depth ($d_1$) of a further surface (7) in the plane (12), measured from an outer periphery ($M_2$) of the base (3) to an outer periphery (M$_1$) of the shaft (4), is from greater than to equal to 0.2 to 4 mm.

13. Scan abutment according to claim 1, wherein the thickness (d$_2$) of the side wall (10) of the shaft (4) varies at the outer periphery of the shaft.

14. Scan abutment according to claim 1, wherein the material of the scan abutment is selected from a polymeric material, filled polymeric material, metal, a fiber-reinforced polymer, an alloy, hybrid material, such as titanium, cobalt chrome, gold, wherein the polymeric material is selected from fluoropolymers, polysulfide-containing polymers, polysulfone-containing polymers, polyaryletherketones, polyimides, PAEK (polyaryletherketones), PC (polycarbonate), PEEK (polyetheretherketones), PEK (polyetherketones), PEKK (poly(etherketoneketones)), PEEEK (poly(etheretheretherketones)), PEEKK (poly(etheretherketoneketones)), PEKEKK (poly(etherketoneether-ketoneketones), PES (polyarylsulfones), PPSU (polyarylsulfones), PSU (poly sulfones), PPS (polyphenylene sulfides), PFA (perfluoroalkoxy polymers), PFE (poly(fluorenylene ethynylene) polymers), PVDF (polyvinylidene fluorides), PCTFE (polytetrafluoroethylenes), PAI (polyamide imides), PI (polyimides), PEI (polyetherimides), PBI (polybenzimidazoles).

15. Method of using a scan abutment according to claim 1, wherein the at least one surface (6) and/or the at least one further surface (7)
    a) is perpendicularly arranged to the central axis of the implant when the scan abutment (2) with its bottom side (8.2) of the base (3) is attached onto the front face (1.1) of the implant (1) for determination of the position (x,y,z-coordinates) of the front face (1.1) of a dental endosseous implant (1), or
    b) the central axis of the scan abutment (2) is coaxially arranged to the central axis of the implant (1), and the one planar surface (6) and/or the at least one further surface (7) is perpendicularly arranged to the central axis of the implant (1).

* * * * *